(12) United States Patent  
Jenkins et al.

(10) Patent No.: US 9,072,822 B2  
(45) Date of Patent: Jul. 7, 2015

(54) SPINAL SHIELD IMPLANT AND TREATMENT OF SPINAL METASTASES

(75) Inventors: Arthur L. Jenkins, Greenwich, CT (US); Jamie Cesaretti, New York, NY (US)

(73) Assignee: ICAHN SCHOOL OF MEDICINE AT MOUNT SINAI, New York, NY (US)

( * ) Notice: Subject to any disclaimer, the term of this patent is extended or adjusted under 35 U.S.C. 154(b) by 1040 days.

(21) Appl. No.: 13/063,356

(22) PCT Filed: Sep. 18, 2009

(86) PCT No.: PCT/US2009/057399  
§ 371 (c)(1),  
(2), (4) Date: Oct. 31, 2011

(87) PCT Pub. No.: WO2010/033756  
PCT Pub. Date: Mar. 25, 2010

(65) Prior Publication Data  
US 2012/0037165 A1 Feb. 16, 2012

Related U.S. Application Data

(60) Provisional application No. 61/098,454, filed on Sep. 19, 2008.

(51) Int. Cl.  
*A61L 31/14* (2006.01)  
*A61N 5/10* (2006.01)  
*A61F 2/30* (2006.01)

(52) U.S. Cl.  
CPC ....... *A61L 31/14* (2013.01); *A61F 2002/30082* (2013.01); *A61F 2002/30672* (2013.01); *A61F 2210/0095* (2013.01); *A61N 5/1027* (2013.01); *A61N 2005/1094* (2013.01)

(58) Field of Classification Search  
CPC ............... A61N 2005/1094; A61N 5/1027; A61N 5/1007; A61N 2005/1011; A61N 2005/1021; A61N 2005/1019; A61M 37/0069; A61M 2210/1003; A61F 2002/30082  
USPC ........ 600/1–8, 37; 606/61, 86, 69, 60, 70–74, 606/249; 128/846, 888  
See application file for complete search history.

(56) References Cited

U.S. PATENT DOCUMENTS

| | | | |
|---|---|---|---|
| 4,208,588 A * | 6/1980 | Rudin | 250/496.1 |
| 5,437,672 A | 8/1995 | Alleyne et al. | |
| 5,496,318 A * | 3/1996 | Howland et al. | 606/249 |
| 6,132,358 A | 10/2000 | Glenn et al. | |
| 2005/0038458 A1* | 2/2005 | Bailly et al. | 606/157 |
| 2005/0177155 A1* | 8/2005 | Alleyne | 606/61 |
| 2006/0047178 A1 | 3/2006 | Winkler et al. | |

* cited by examiner

*Primary Examiner* — Christine H Matthews  
(74) *Attorney, Agent, or Firm* — Leason Ellis LLP

(57) ABSTRACT

A radiation shield for use in treating spinal metastatic disease is formed of a body that is configured to surround the spinal cord and includes a section that can be axially extended for increasing the surface area of the shield.

21 Claims, 6 Drawing Sheets

SPINAL SHIELD IMPLANT AND TREATMENT OF SPINAL METASTASES

CROSS-REFERENCE TO RELATED APPLICATION

This is a U.S. national phase application under 35 U.S.C. §371 of International Patent Application No. PCT/US2009/057399 filed Sep. 18, 2009, which claims the benefit of U.S. patent application Ser. No. 61/098,454, filed Sep. 19, 2008, which is hereby incorporated by reference in its entirety. The International Application was published on Mar. 25, 2010 as WO 2010/033756 A1 under PCT Article 21(2).

TECHNICAL FIELD

The present invention relates in general to a device for use in treating proliferative tissue disorders and, in particular, relates to an apparatus and a method of treatment of such disorders that occur in the vicinity of the spinal cord by the application of radiation.

BACKGROUND

As is well known, the spinal cord is part of the central nervous system and is connected to the brain. From the brain, the cord runs down the back and is surrounded by and protected by the bony vertebral column. The cord is surrounded by fluid called "cerebral spinal fluid," that acts as cushion to protect the delicate nervous tissues. The cord itself consists of millions of nerve fibers that transmit information to and from the limbs, trunk and organs of the body. Nerves which are typically called the spinal nerves or nerve roots come off the spinal cord and pass out between the vertebrae to carry information from the spinal cord to the rest of the body.

Cervical nerves, which are nerves in the neck, supply movement and feeling to the neck and upper trunk; thoracic nerves, which are nerves in the upper back, supply the trunk and abdomen; and lumbar and sacral nerves, which are nerves from the lower back, supply the legs, the bladder, bowel and sexual organs. The spinal nerves carry information from different levels (segments) in the spinal cord and the nerves and segments in the spinal cord are numbered in the same way. Accordingly, the cervical nerves and spinal cord segments are identified as C1-C8, the thoracic and lumbar are T1-T12 and L1-L5 and the sacral are S1-S5.

Metastatic disease occurs when cancer from one site in the body spreads to another area. The spine is a common area for the spread of cancer and can cause a variety of neurological and bone related symptoms. A number of studies have found that between about 30% to about 70% of cancer patients had spinal metastases when autopsies were conducted. Metastases to the spinal column and spinal cord commonly originate from cancers occurring in the lung, breast, gastrointestinal tract, prostrate and lymphomas. Metastases to the spine are primarily treated in order to control pain, maintain or restore stability, and to preserve or restore function as much as possible.

Some of the different treatments for treating the metastases include radiotherapy and surgical radical resection. In addition, a decompressive laminectomy can be performed in which a portion of the vertebral bone called the lamina is removed. There are many variations of laminectomy and typically, the traditional procedure excises much more than just the entire lamina in that the entire posterior backbone is removed, along with overlying ligaments and muscles. The lamina is a posterior arch of the vertebral bone lying between the spinous process, which juts out in the midline, and the more lateral of each vertebra. The pair of lamina, along with the spinous process, makes up the posterior wall of the bony spinal canal. The lamina is typically removed in order to allow the surgeon access to deeper tissues inside the spinal canal, to perform a direct decompression for dorsally located lesions, or an indirect decompression for lesions that are in front of the spinal cord (allowing the spinal cord to fall away from the lesion).

Another approach surgeons use to treat spinal metastases is a transpedicular approach, which is popular when the tumor involves the dorsal or lateral aspect of the vertebral body, especially when the disease extends into the pedicle and associated dorsal elements. Facetectomy coupled with pedicle resection allows access into the vertebral body. Often coupled with rigid instrumentation above and below, this procedure provides an excellent surgical result.

Whereas primary prostrate tumors are treated with much higher doses of radiation (either as fractionated external beam radiation, say, with 85 Gy or a combination of directly implanted radioactive brachytherapy seeds, say, providing 100 Gy and local fractionated radiation for 45 Gy), spinal metastases are currently treated by doses on the order of 30-55 Gy of fractionated external beam radiation, which is less effective than the higher doses but is limited primarily because of concern about radiation induced myelopathy (damage to the spinal cord) seen with higher doses of radiation.

One other deficiency of traditional radiation treatment to spinal pathology is the problem of primary or secondary epidural tumors in the spine recurring after initial resection and external fractionated radiotherapy. Given the confines of the surgical site, adequate local excision with wide margins is difficult to perform. In view of the foregoing, postoperative irradiation is a valuable adjuvant treatment; however, irradiation of the spine has specific limitations that often result in inadequate tumor dose. It has been suggested that shielding of the spinal cord may permit greater radiation doses to be safely delivered by brachytherapy to recurrent tumors. Brachytherapy, also referred to as sealed source radiotherapy or endocurietherapy, is a form of radiotherapy where a radioactive source is placed inside or next to the area requiring treatment. The sealed radioactive source is also commonly referred to as a "seed" and/or "source." However, the shielding that has been proposed, such as in Hamilton, Lula et al., Int. J. Rad One Biol Physics 32(2) 507-511, 1995, has a number of disadvantages that limits its use and effectiveness. In particular, the shield was made of a simple foil material and was used in the epidural plane and did not have a particular contour that would assist in placement and the effectiveness of the shield when placed between the spinal dura and spinal vertebral body. In addition, this type of foil shield had other limitations in that the shield was placed on the dorsal surface of the cord, whereas the roots prevented placement of the shield ventral to the cord. The shield was also used after a multiply-recurrent tumor was re-resected using a large standard "open" technique in only one very young patient in what seemed a less than rigorous manner. Yet another disadvantage of the foil technique is that the foil scatters back the radiation and this scattering can be random.

There is no significant current utilization of implanted radioactive seeds and there are only scattered references to intraoperative doses of brachytherapy, none involving the concomitant use of seeds and bone cement.

There is consequently a need for a shield or the like that is specifically contoured for placement between the spinal dura and the spinal vertebral body and be able to be implanted through either an open or a minimally invasive technique in order to shield the spine from all sources of radiation across the electro-magnetic spectrum.

SUMMARY

According to one embodiment of the present invention, a method for treating spinal metastatic disease includes the steps of: removing a pedicle in order to gain access to a spinal canal; resecting a tumor that is accessible through the spinal canal; applying radiation to a location where the tumor was resected; and placing bone cement in a location where the pedicle was removed, wherein the cement contains at least one radioactive seed implant. The method can further include the steps of: implanting a shield about a spinal cord that is in the spinal canal; and positioning the shield so that the shield is between the radioactive seed implant and the spinal cord, clear of the nerve roots.

The present invention also relates to a radiation shield for use in treating spinal metastatic disease. The shield is formed of a body that is configured to surround the spinal cord and includes a section that can be axially extended for increasing the surface area of the shield. The body is also configured to accommodate spinal cord nerves when implanted. The body can be formed of separate first and second parts that are detachably coupled to one another (e.g., in a tongue and groove manner). The section that can axially extend can be a third part that is separate from the first and second parts and can be manually movable from a fully retracted position to a fully extended position, or can be separate but attached and slide into position from within the confines of the first or second part. The third part is guided within at least one guide slot formed in the first part to allow axial extension of the third part relative to the first part. By positioning the third part in the fully retracted position, the shield can be more easily placed in the spinal cord canal and can negotiate better around the spinal cord nerves and then the third part can be axially extended when the shield is located in the desired position relative to the spinal cord and the radioactive seed implant. In a further aspect, a radiation shield can include a portion that extends into an axially extended position using an integral mechanical assist or in response to a thermal trigger, electrostatic, magnetic, or other direct or indirect force applied to the device.

BRIEF DESCRIPTION OF DRAWING FIGURES

DETAILED DESCRIPTION OF EMBODIMENTS

Figure 1:
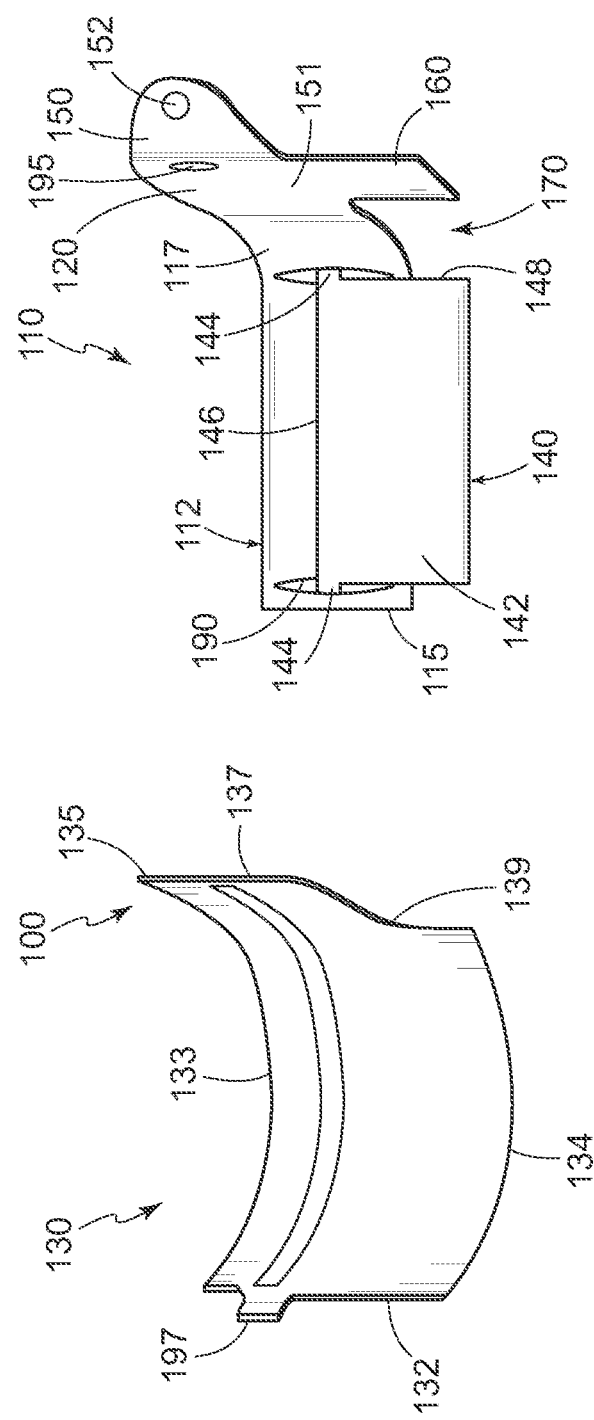
FIG. 1 is an exploded perspective view of a spinal shield in accordance with one embodiment of the present invention.
Figure 2:
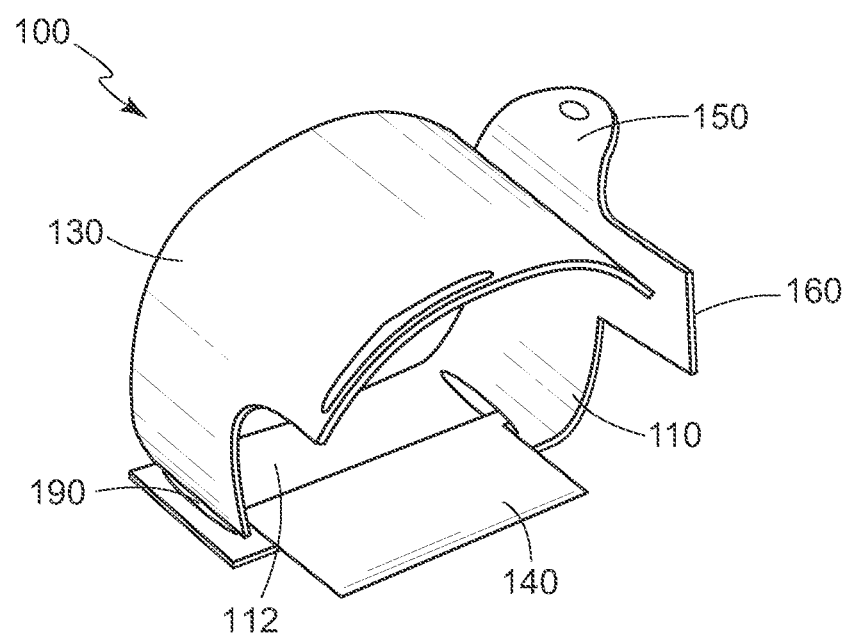
FIG. 2 is a perspective view of the spinal shield of FIG. 1 in an assembled state.
Figure 3:
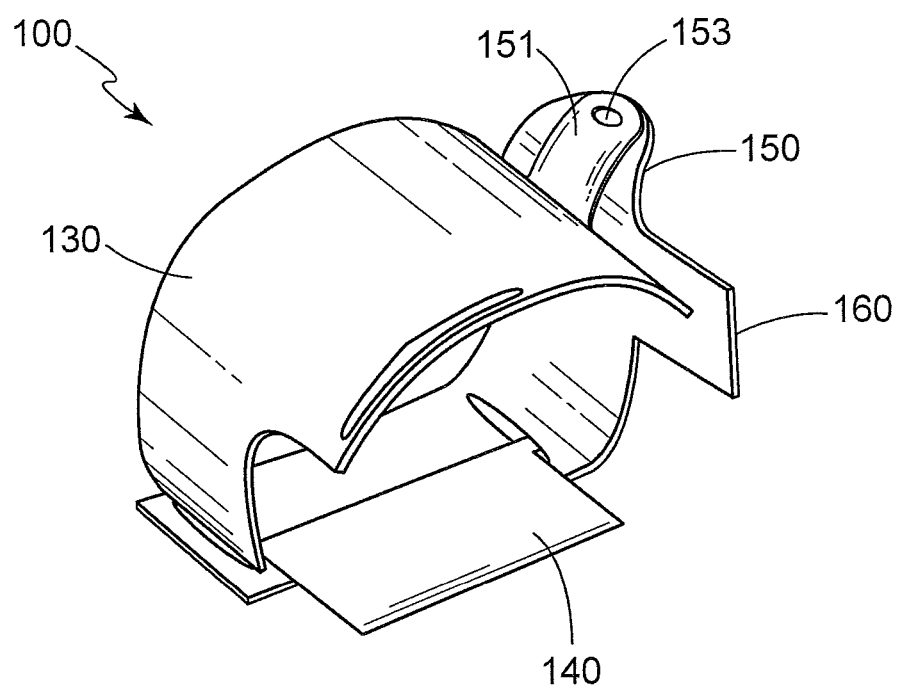
FIG. 3 is a perspective view of the spinal shield of FIG. 1 in an assembled state and according to another embodiment.

FIGS. 1-2 illustrate a radiation shield 100 for use in treating spinal metastatic disease according to a first exemplary embodiment. FIG. 1 illustrates the shield 100 in a non-assembled state showing the various components of the shield 100 and FIGS. 2-3 illustrate the shield 100 in an assembled state.

The shield 100 in this embodiment is formed of two complementary parts that are coupled together to form the assembled shield 100 shown in FIG. 2. The shield 100 includes a first component 110 and a second component 130 that is configured to mate with the first component 110 to form the assembled shield 100. The first component 110 can be thought of as a base section, while the second component 130 can be thought of as a cover.

The first component 110 includes a first section 112 and a second section 120 that extends outwardly (axially) outward from the first section 112. The first section 112 can be generally planar or it can have a slight curvature. The second section 120 can be formed to have a slight curvature and is generally formed so that it at least includes a portion that is perpendicular to the first section 112. The first and second sections 112, 120 are typically integral with one another and are formed as a single shield piece. The first section 112 has a generally rectangular shape.

The first component 110 is also formed so that a portion or member thereof 140 thereof is extendable and retractable in an axial direction, thereby allowing the first component 110 to have a non-deployed state where the member 140 is retracted and a deployed state where the member 140 is extended. When the member is retracted, the shield 100 has an insertion configuration for advancement around the spinal cord clear of the nerve roots. When the member 140 is fully deployed, the surface area (coverage) of the shield 100 is increased, thereby allowing the shield 100 in its implanted position to shield more of the spinal cord, and not impact adjacent nerve roots. In the illustrated embodiment, the member 140 is in the form of an axially deployable slide-out structure that can be moved between a fully retracted position in which it at least substantially overlies the first section 112 and a fully extended position in which only a portion thereof overlies the first section 112 and a majority thereof extends beyond the first section 112.

The member 140 includes a base section 142 that is movable in an axial direction relative to the first section 112 to allow the member 140 to move between the fully extended and fully retracted position. The base section 142 includes structures that allow it to be controllably moved between the fully retracted position and the fully extended position. For example, the base section 142 can include a pair of prongs or tabs 144 that are formed at or near an inner edge 146 of the member 140. The tabs 144 can be a pair of upstanding structures that extend not only upward but also are formed so that they extend outwardly from opposing side edges 148 of the base section 142. The base section 142 thus has a maximum width in the area where the tabs 144 are formed.

The tabs 144 are typically integrally formed with the base section 142 and can be in the form of a pair of bent, upstanding tabs of the base section 142. In the illustrated embodiment, the member 140 is generally planar; however, it can contain a slight curvature.

The first section 112 has complementary slots 190 to allow the member 140 to move in a controlled, guided manner between the fully retracted position and the fully extended position. The slots 190 are elongated slots that extend between a first edge 115 of the first section 112 and an opposite end region 117 of the first section 112 where the first and second sections 112, 120 join. The region 117 is near the location where the second section 120 extends upwardly from the first section 112. The width of the slots 190 is such that a tab 144 can be received therein for coupling the member 140 to the base section 142, while permitting the member 140 to travel axially from the fully retracted to the fully extended position as described herein. More specifically, the member 140 is coupled to the base section 142 by inserting the tabs 144 into the slots 190 such that the tabs 144 are disposed along an outer surface of the first component 110. In other words, the tabs 144 can be inserted into the slots 190 and be latched to the base section 142 by locating the tabs 144 along the outer surface of the first component 110. Alternatively, the slots 190 can have an enlarged entrance section that receives the tabs 144 and then the member 140 is moved forward into the reduced width portions of the slots 190 to effectively capture the member 140 and guide the member 140 as it is moved axially between the retracted and extended positions.

A free side edge 115 of the first section 112 can be slightly curved to permit the first and second components 110, 130 to fit together in a clean manner that presents an atraumatic surface to the patient.

During use, as described below, the member 140 is moved axially using a tool or the like (not shown). For example, after the first component 110 is laid in its proper, desired location at the surgical site, a user can deploy the member 140 by using a tool, e.g., a hook member, that engages the member 140 such that when the user manipulates the tool, e.g., moving it in a axial direction, the member 140 is driven from one position to another position. This permits the member 140 to expand the overall coverage area (shield area) of the first component 110. The fully extended position is reached when the member 140 reaches one end of the slots 190.

It will be appreciated that other coupling techniques can be used to couple the member 140 to the base section 142 to allow the axial movement of the member 140 from the fully retracted to fully extended position. For example, a locking pin and groove concept can be employed or other techniques can be employed as described below.

The second section 120 also includes a tab or finger 160 that extends axially outward from the second section 120. The tab 160 and second section 120 generally define an L-shape structure and when the member 140 is in the deployed state, there is a cut-out or opening 170 formed between the tab 160, the member 140 and the second section 120. The cut-out 170 is thus formed along one side of the shield 100 when the member 140 is in the deployed state. As described below, the cut-out 170 accommodates the spinal cord nerves that pass axially outward from the spinal cord itself when the shield 100 is in its implanted position.

The second section 120 includes a flange 150 that can be used for securely attaching or coupling the first component 110 to a bone in the surgical site. For example, the flange 150 can be in the form of a bent portion of the section 120 that is angled relative to a wall 151 that defines the second section 120. The flange 150 includes a means for being coupled to the bone and in the illustrated embodiment, the flange 150 includes an opening 152 through which a fastener (not shown) is received in order to securely attach the first component 110 to the bone at the surgical site. The flange 150 extends axially outward in a direction away from the first section 112.

The second component 130 is configured to mate with the first component 110 so as to create an assembly that generally has a circumferential shape and has a central opening or space 101 therebetween to accommodate the spinal cord and dura mater that surrounds the spinal cord as described below. The second component 130 is thus generally in the form of a cover or the like that completes the first component 110. The second component 130 has a curved shape, e.g., semicircular shape, that includes a first end 132 and an opposing second end 134 and first and second side edges 133, 135. The first end 132 is a generally straight edge, while the second end 134 has a straight portion 137 but also includes a cut-out portion 139. The cut-out portion is defined by a curved edge 139 that is joined at one end to the straight portion 137.

When the first and second components 110, 130 mate together, the cut-out 139 defines an opening that accommodates the spinal cord nerves similar to and complementary to the cut-out 170 which is located opposite. The cut-outs 139, 170 thus define two opposite openings through which the spinal cord nerves can pass, thereby allowing the shield 100 to be inserted into the surgical site and in a position where the shield is disposed about the dura mater of the spinal cord.

The second component 130 is designed to be removably coupled to the first component 110 to complete the shield 100. For example, a hinge or similar coupling structure can be formed to allow the first and second components 110, 130 to be coupled to one another. In this embodiment, the first component 110 can include a coupling slot or groove 195 that is formed in the second section 120 and in particular, the slot 195 is formed below where the second section 120 is bent to form the flange 150. The slot 195 is an elongated longitudinal slot that is formed in the second section 120.

The second component 130 has a complementary coupling structure that engages the slot 195 to couple the first and second components 110, 130 to one another. For example, the second component 130 can include a tongue or latch 197 that is configured to be inserted into the slot 195. The tongue 197 can be in the form of a tab or protrusion that extends outwardly from the first end 132. For example, the tongue 197 can have an L-shape with the shorter side of the L being the section that is connected to the first end 132. The second component 130 is configured such that that when it is coupled to the first component 110 by inserting the tongue 197 into the slot 195, the straight portion 137 can sit on the base section 142 (at the end opposite the second section 120). In this position, the first and second components 110, 130 are assembled and form a structure that can circumferentially surround an object (e.g., spinal cord and the dura mater) that is disposed through the central opening or space defined between the first and second components 110, 130.

The straight portion 137 can sit on a portion of the base section 142 that lies outside the slot 195 and therefore, does not interfere with the axial movement of the member 140. In other words, the member 140 can be moved axially between the fully retracted position and the fully extended position as described herein. Alternatively, the straight portion 137 can be positioned adjacent the end of the base section 142 and be supported by an underlying structure, such as a bone or the like. In either embodiment, the two components 110, 130 form at least generally a circumferential structure that has a central opening or space that is sufficient size to accommodate the spinal cord and dura matter about which the shield 100 is disposed.

As shown in FIG. 3, the second component 130 (cover) can also include a flange 151 that can be used for securely attaching or coupling the second component 130 to the bone in the surgical site. Similar to the flange 150, the second flange 151 is a portion (tab) of the cover 130 that protrudes outwardly and is configured to be complementary to and mate with the flange 150 of the first component 110. For example, when the second component 130 is mated with the first component 110, the second flange 151 overlies the flange 150 to allow both flanges 150 to be securely attached to the underlying bone. As with the flange 150, the second flange 151 includes a means for being coupled to the bone and in the illustrated embodiment, the second flange 151 includes an opening 153 through which a fastener (not shown) is received in order to securely attach the second component 130 to the bone at the surgical site. To securely attach the assembled shield 100 in this embodiment, the two components 110, 130 are mated together which results in the flanges 150, 151 overlying one another and the openings 152 are in registration with one another. The fastener is then inserted through the openings 152, 153 into the bone, thereby providing a local attachment between the shield 100 and the bone.

The first and second components 110, 130 of the shield 100 are formed of a suitable material that shields the spinal cord to permit greater radiation doses to be safely delivered by high, intermediate and low dose rate brachytherapy, nuclear particle beam therapy and photon beam therapy to both recurrent and newly diagnosed tumors. For example, the shield 100 is formed of a thin, flexible metallic structure of a dense but inert material such as tantalum or gold. The material of the shield 100 has the properties that it interacts minimally with higher-energy photons of external beam radiation (which can be used in combination with local radioactive seed implants), but effectively protects the spinal cord from the on-going radiation of the implanted seeds. In this manner, the total dose to the tumor can be dramatically increased, without the spinal cord seeing a significant increase in exposed radiation. The material can also be modulated by applying surface coatings, which would specifically promote and inhibit interactions with neutrons, protons, heavy nuclear particles, electrons and photons should the therapeutic team have these modalities available to compliment the brachytherapy boost dose.

Figure 6A:
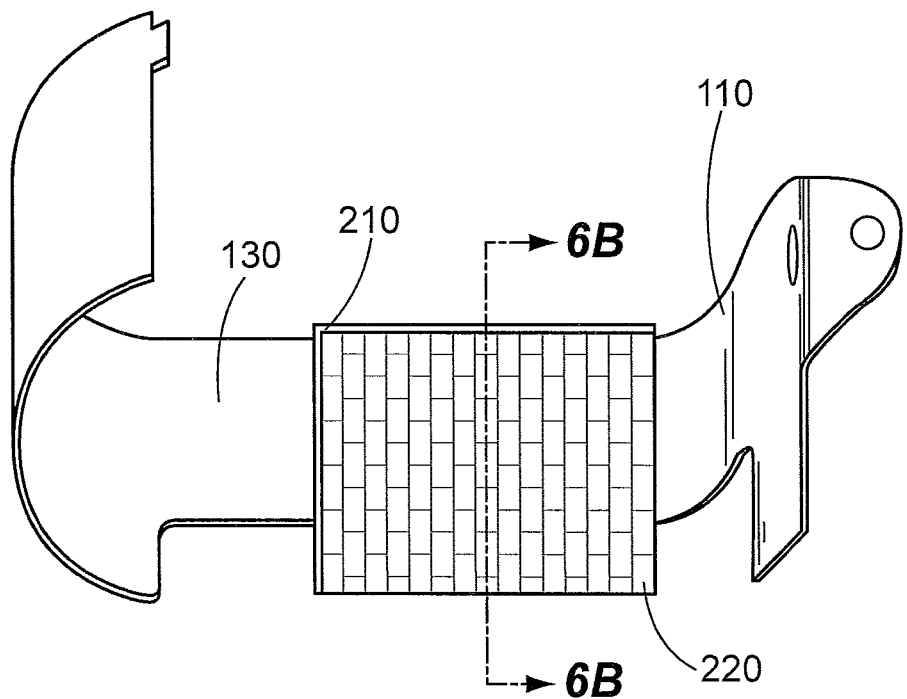
FIG. 6A is a perspective view of spinal shield according to another embodiment.
Figure 6B:
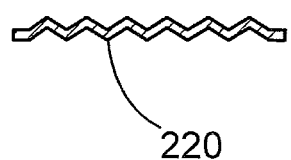
FIG. 6B is a cross-sectional view taken along the like 6B-6B.

In yet another embodiment, shown generally in FIGS. 6A and 6B, the extendable/retractable portion of the shield 100 can be formed using a temperature, electrical, magnetic, or other exogenous stimulus-responsive material that allows a controlled extension and retraction of a portion of the shield 100 under given conditions, or expansion in a single direction without expanding in other directions, like some of the newer exotic metamaterials. For example, a portion of the first component 110 can be formed of a shape memory alloy, such a nickel-titanium alloy, that allows a change in structure of the first component 110 based on a temperature change that the first component 110 experiences when implanted and subjected to body temperature. NiTi alloys can include tertiary elements in trace to small amounts to further control the shape memory effect and superelasticity. The driving force behind these properties is a reversible solid-state phase transformation from austenite to martensite on cooling (or by deformation) and the reverse transformation from martensite to austenite on heating (or upon release of a restraining force).

More specifically, the first component 110 can be constructed to include a portion that is formed of a shape memory alloy and in particular, the movable member 140 that moves between the fully retracted position and the fully extended position is formed of this material. For example, a base section 210 or a separate extendable section 220 that is similar to the movable member 140 in that it can move axially so as to increase the effective shield coverage of the first component 110 can be formed of NiTi alloy. For ease of illustration, the embodiment where the section 220 that is separate from the base section 220 is the component that extends axially under select conditions will be described herein; however, other embodiments are equally possible including one where the base section 220 is formed of a shape memory alloy.

The extendable section 220 is formed in part of a shape memory alloy and is constructed to have a bellows construction at least in one state. One edge of the extendable section 220 is secured (e.g., bonded) to the base section 220. In order to form a bellows structure, a shape memory alloy sheet can be laser etched and then trained into bellows at a low temperature. The bellows structure can be defined by a plurality of bellows strips that are joined and coupled to one another by a plurality of links that permit the movement of the section between a fully retracted position where the section 220 assumes the bellows construction and a fully extended position where the section assumes more of a planar construction due to "flattening" of the shape memory alloy that fours the section 220. The extendable section 220 also includes a shield layer that is positioned over the bellows structure and is constructed to accommodate the axial movement of the extendable section 220. The shield layer is designed to effectively shield the spinal cord from the radiation emitted from the brachytherapy seeds and is typically formed of a suitable metal. The shielding layer could be modified to have an acrylic, silicon, plastic or heavy metal component to be better visualized by modern image guided modalities used in daily radiation therapy practice; however, inclusion of this material does not materially alter the shielding properties of the shield. In other words, the shield still performs its intended function. For example, the shield layer can be in the form of a gold foil or the like. Gold foil has a degree of malleability and therefore, can accommodate both the extension and the retraction of the extendable section 220. The gold foil or similar structure can be applied using any number of different techniques including a spray coating technique where a layer of gold is laid down over the shape memory alloy bellows structure, or the gold layer can be applied using other bonding techniques.

Accordingly, the first component 110 is formed such that at low temperatures, the extendable section 220 assumes the fully retracted position to allow implantation into the body at the surgical site as described below. However, the exposure of the first component to higher temperatures (e.g., body temperature) causes the extendable section 220 to extend axially outward to the fully extended position. The shape memory alloy used to make the section 220 is designed so that the extendable section 220 has a bellows structure at low temperatures, while at higher temperature, including body temperature, the section 220 "flattens" out in that its length increases as it become more planar in nature. This eliminates the need for a separate tool to increase the axial coverage of the shield when the shield 100 is implanted. Instead, the temperature of at least the first component 110 is controlled (e.g., maintained at lower temperatures) prior to implantation. This causes the extendable section 220 to be maintained in a fully retracted position. As the shape memory alloy is exposed to warmer temperatures, the section 220 flattens out in an axial direction as described herein, thereby increasing the coverage of the shield 100. In other words, the self expanding nature of the shape memory alloy provides another means for increasing the axial coverage of the first component 110 after it has been implanted into the surgical site.

Another iteration of this expandable design would be a device that is made of a material that is made up of a web of carbon nano-tubules that can change orientation with an electrical or magnetic stimulus, shifting the orientation of the materials allowing them to swing into a lower, longer, or altered configuration.

Figure 4:
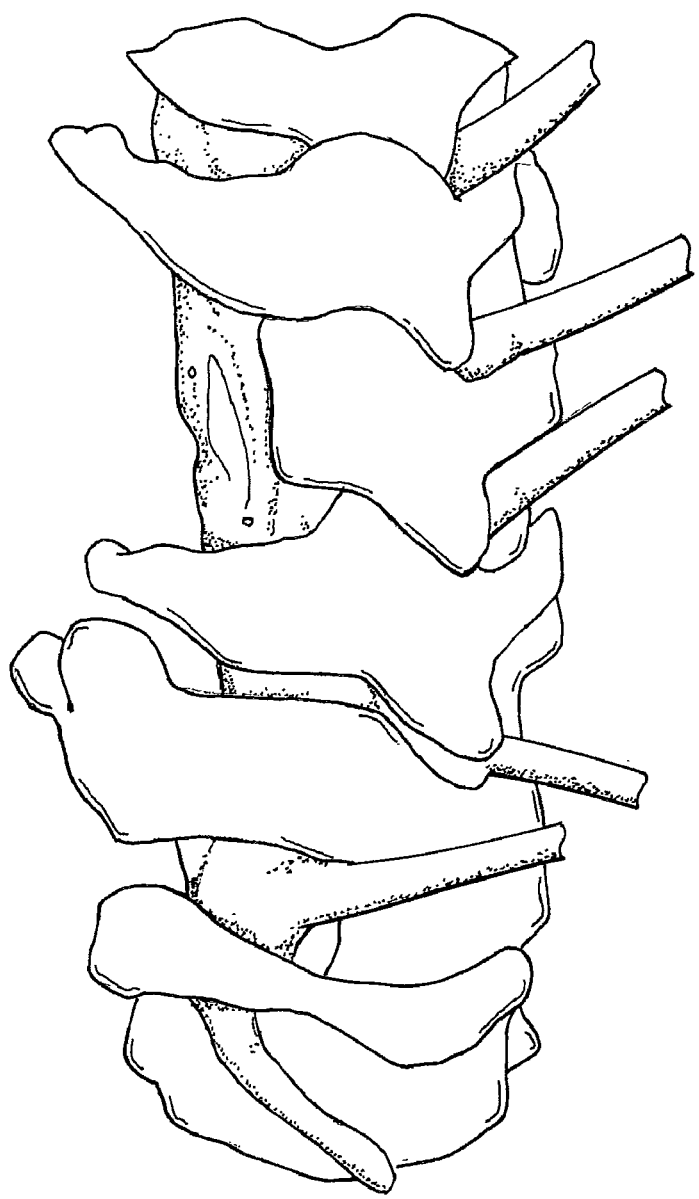
FIG. 4 is a perspective view of the spinal cord area showing removal of a bone to access the spinal cord.

An exemplary method of using the shield 100 for treatment of spinal metastases by application of radiation is now described. Surgical resection of a tumor typically first involves removal of a target pedicle as shown in FIG. 4. The pedicles are two short, thick processes, which project backward, one on either side, from the upper part of the body, at the junction of its posterior and lateral surfaces. The pedicle is thus a segment between the transverse process and the vertebral body and is often used as a radiographic marker and an entry point in several surgical procedures. Surgical resection of the tumor is performed by removing as much of the tumor as possible from the front of the spine by accessing it from the rear of the spine. After removal of as much of the tumor as possible, the surgeon than performs brachytherapy by implanting at least one radiation source in the surgical site. In the past, after resection of the tumor, cement was placed in the location where the pedicle was removed (transpedicular approach) and traditional brachytherapy involved implanting radiation sources (seeds) directly into the tissue to be treated.

However, in accordance with one exemplary surgical procedure of the present invention, the radiation source is placed directly into the cement that is used to replace the resected bone (pedicle). In particular, the radiation source can be in the form of radioactive brachytherapy seeds that are implanted directly into the cement and thus, are contained within the cement at the surgical site. Any number of different cements can be used so long as they are intended for this type of application. One exemplary cement that can be used is Stryker Simplex Bone Cement. Similarly, any number of different radiotherapeutic sources can be used and in particular, the source can be brachytherapy seeds, such as Onco-Seed™ type seeds commercially available from Nycomed Amersham Imaging.

The shield 100 of the present invention is designed to effectively shield the spinal cord from the radiation that is emitted from the brachytherapy seeds and a teleradiotherapy boost. The shield 100 is implanted into the surgical site by first placing the first component 110 around a circumferential portion of the spinal cord. The configuration of the first component 110 is designed to follow the contour of the spinal cord area. The first component 110 can be implanted into the surgical site by placement of the first edge 115 into the spinal dura and spinal vertebral body, thereby allowing placement of the first component 110 underneath the spinal cord. The first component 110 is thus manipulated while being inserted such that the first component 110 is disposed about a circumferential portion of the spinal cord and dura matter. Since the tumor resection occurs by removing the tumor from the front by accessing it from the rear, the first component 110 is implanted and directed (slid) toward the front of the spinal cord area to the position described above where the base section 142 and second section 120 of the first component 110 are positioned facing the dura mater.

A tool can be used to assist in placement of the first component 110 and second component 120 for that matter in the spinal cord surgical site. For example, a tool that can grasp a portion of the component can be used to place the component into the surgical site. The tool can be a tong-like structure or the like that allows a user to grasp and insert the held component into the surgical site.

In one embodiment, the thickness of the shield 100 is about 1 mm to about 2 mm; however, other thicknesses are possible.

Once the first component 110 is in the target implanted position and it is free of the nerve roots of the spinal cord, the axially extendable section of the first component 110 is deployed to the fully extended position. The deployment can occur using one of the techniques disclosed herein (e.g., using a tool or by forming the extendable section with a temperature responsive material) or by employing other techniques. The extendable section thus extends out axially to the fully extended position, thereby increasing the effective axial shielding coverage of the shield 100 about the spinal cord and dura mater without adversely impacting the nerve roots. The cut-out 170 that is defined between the extended base section 142 and the tab 160 receives and accommodates the spinal cord nerves such that they exit the spinal canal unencumbered. The first component 110 thus is constructed so that it can be safely and effectively implanted in the interstitial spinal cord area while the spinal cord nerves remain in place and unencumbered. In other words, the first component 110 is inserted into the spinal cord surgical site in its fully retracted position to allow the first component 110 to pass by and free of engagement with the nerve roots that are located at the surgical site.

In order to prevent migration of the shield 100 about the spinal cord, the flange 150 is positioned proximate (e.g., in an abutting relationship) an anchoring surface, such as a bone surface, and the fastener is passed through the opening 152 and anchored into the bone, thereby securely attaching the first component 110 to the bone. By anchoring the flange 150 to the bone, the assembled shield 100 is maintained in the desired position and any unwanted migration of the shield 100 is eliminated. The fastener can be in the form of a bone screw or the like or some other type of fastener that can attach the shield 100 to the bone.

To complete the shield 100 assembly, the second component 130 is mated with the first component 110. The second component 130 is coupled to the first component 110 by inserting the tongue 197 into the slot 195 resulting in the first and second components 110, 130 being coupled to form a structure that circumferentially surrounds the spinal cord and the dura mater that is disposed through the central opening or space defined between the first and second components 110, 130. In addition, the nerve roots of the spinal cord are accommodated since the nerve roots can pass through the opposing cut-outs 170, 139.

The spinal cord is thus completely surrounded by the assembled shield 100 in the area where the brachytherapy seeds are implanted and this allows a higher dose of radiation to be employed in the brachytherapy treatment of recurrent tumors. In addition, when the shield is completely deployed the components of the shield can be easily visualized by image guided teleradiotherapy devices.

Alternatively, the cement with the brachytherapy seeds can be placed into the surgical site after the shield 100 has been installed about the spinal cord and dura mater. In other words, the first component 110 can be laid in the target location about a circumferential portion of the spinal cord and dura mater and the second component 130 can be securely coupled to the first component 110, as described above, so as to circumferentially surround the spinal cord and dura mater. After the extending section of the first component 110 is fully extended using one of the techniques disclosed herein or another technique, the cement with the brachytherapy seeds is then placed in the location where the pedicular was removed.

In addition, it will be appreciated that instead of having two separate components, the shield 100 can be formed as a single hinged part that can be opened to allow implantation into the spinal cord surgical site and placement of a portion thereof about the front of the spinal cord and dura mater. The shield is then closed by pivoting the "cover" section closed around the spinal cord and dura mater. In each embodiment, the shield is designed to accommodate and let the nerve roots exit the spinal canal unencumbered.

The shield 100 of the present invention provides a number of advantages and allows for a great deal of flexibility in performing surgical resection of tumors in the spinal canal. The tumor is resected and then the radiotherapy source (brachytherapy seeds) and shield are implanted into the target spinal area. As discussed above, the shield can be implanted prior to implanting the radiotherapy source or the radiotherapy source can be implanted prior to implanting the shield. Due to the robustness of the shield 100 and the ability to place the shield 100 in a specific target operative site, increased dosage levels of radiation can be used. In addition, the shield itself can serve as a physical barrier to protect the cord should brachytherapy and teletherapy fail to control the peri-spinal tumor.

Figure 5:
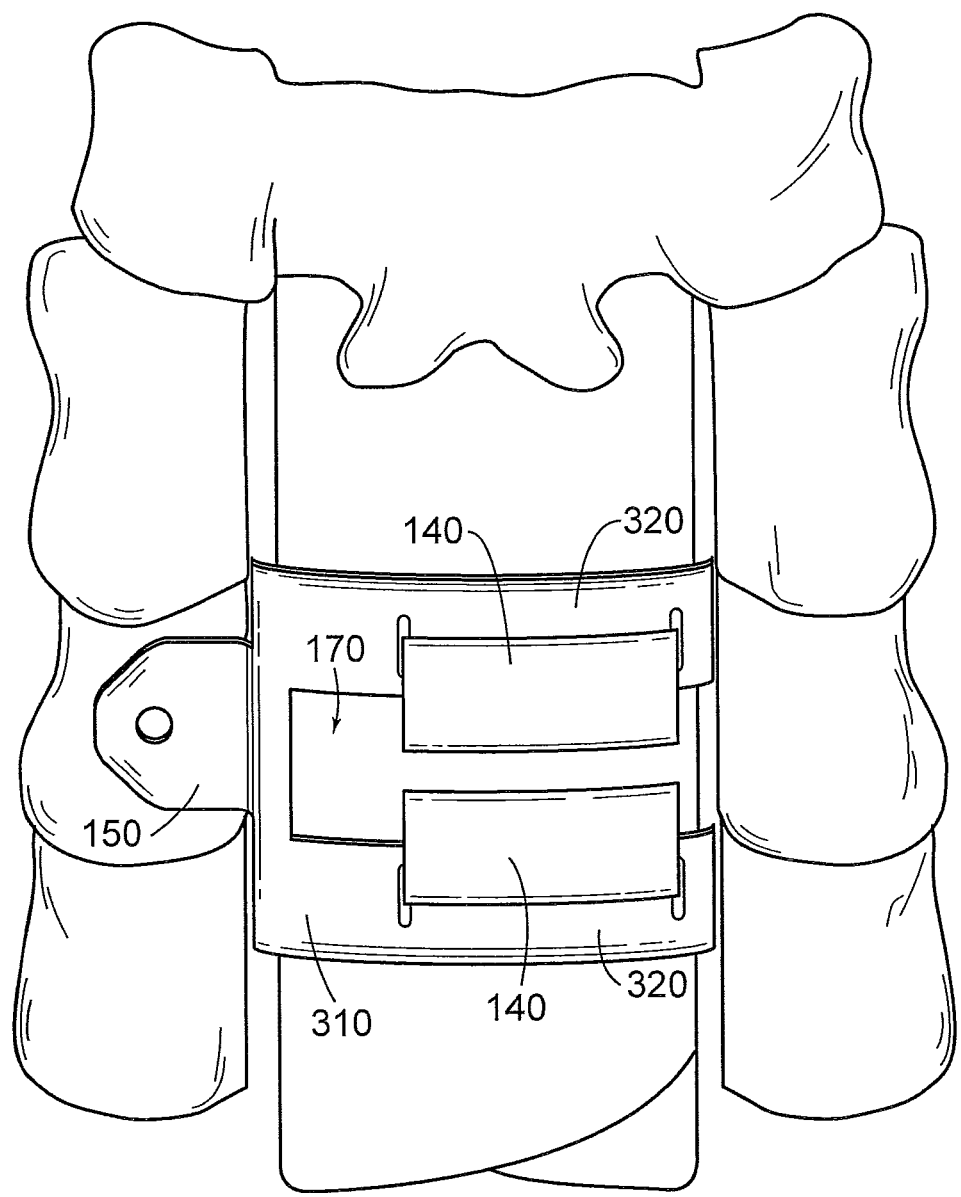
FIG. 5 is a base part of a spinal shield in accordance with another embodiment.

FIG. 5 shows yet another embodiment of a spinal shield 300 that includes a first component 310 and a cover (not shown) that can be similar to the second component 130. In this embodiment, the first component 310 is similar to the first component 110 with the exception that it includes two axially movable members 140. The first component 310 is formed such that it includes two finger sections 320 that formed a floor of the first component 310 with a space 330 being formed therebetween. Each of the finger sections 320 includes a movable member 140 that face another and are designed so that during use and when they are axially extended, they move toward another and cover over the space 330, thereby effectively increasing the coverage of the shield 300. Cut-out 170 is present to accommodate nerve roots. As with the first embodiment, the movable member 140 can move within a guide slot as in FIG. 1 or it can move axially using another means. The member 140 can move manually as by using a tool or it can move automatically under select conditions as in the case of it being formed of a shape memory alloy.

It will also be appreciated that the shield of the present invention is not limited to being used at a location where a pedicle bone was removed. Instead, the shield can be implanted at any location along the spinal cord where a radioactive source is implanted proximate the spinal cord and shielding is desired and the shield can be properly implanted about the spinal cord. The removal of the pedicle is merely one exemplary procedure where the shield is used and the radioactive source is placed in bone cement that replaces the removed pedicle. Moreover, the bone cement with the radioactive source implanted therein is not limited to being used only at a location where a pedicle was removed; but rather, the cement can be used at any location where a bone segment is removed or at a location where bone cement is typically used to perform an intended function.

While the invention has been described in connection with certain embodiments thereof, the invention is capable of being practiced in other forms and using other materials and structures. Accordingly, the invention is defined by the recitations in the claims appended hereto and equivalents thereof.

What is claimed is:

1. A radiation shield for use in treatment of a patient having spinal metastatic disease comprising:
a body that defines a hollow space that is configured to receive a spinal cord of the patient such that the body surrounds the spinal cord of the patient, the body including an axially extendable section that is slidably adjustable along a surface of the body so as to increase a surface area of the shield by extending the extendable section in a longitudinal direction relative to the body and the spinal cord resulting in a greater length of the patient's spinal cord being shielded, the body being shaped to accommodate spinal cord nerves when implanted.

2. The radiation shield of claim 1, wherein the body is formed of separate first and second parts that are detachably coupled to one another.

3. The radiation shield of claim 2, wherein the first and second parts are coupled to one another in a tongue and groove manner.

4. The radiation shield of claim 2, wherein the first and second parts are hingedly coupled to one another.

5. The radiation shield of claim 2, wherein the extendable section comprises a third part that is separate from the first and second parts and is manually movable from a fully retracted position to a fully extended position, the third part being guided within at least one guide slot formed in the first part to allow axial extension of the third part relative to the first part.

6. The radiation shield of claim 2, wherein at least one of the first and second parts has a flange that extends axially outward therefrom, the flange including an opening through which a fastener passes for coupling the part to a bone proximate the spinal cord.

7. The radiation shield of claim 6, wherein each of the first and second parts includes an opening which are axially aligned when the first and second parts are assembled to allow the fastener to pass therethrough to securely attach the assembled first and second parts to the bone.

8. The radiation shield of claim 1, wherein the body is formed of tantalum or gold.

9. The radiation shield of claim 1, wherein the body is contoured to sit between the spinal dura and spinal vertebral body, conform to local anatomy and be capable of surrounding the spinal cord on one side between the cord and dura and a radioactive source implanted in the bone of the vertebral body.

10. The radiation shield of claim 1, wherein the body has a thickness between about 0.1 mm and 0.2 mm.

11. The radiation shield of claim 1, wherein the axially extendable section is slidingly adjustable along a height of the body.

12. The radiation shield of claim 1, wherein the axially extendable section has a first end that is coupled to a first part of the body and an opposite second end is coupled to the first part of the body, whereby the axially extendable section slidingly travels in the longitudinal direction along the first part so as to alter an overall height of a structure defined by a combination of the first part and the extendable section.

13. The radiation shield of claim 1, wherein the body that receives and surrounds the spinal cord includes a bottom edge, the axially extendable section moves between a retracted position and an extended position in which the axially extendable section is disposed below the bottom edge.

14. The radiation shield of claim 2, wherein the first part has a convex shape and the second part has a convex shape so as to form a generally circular shaped shield when the first and second parts are coupled to one another.

15. The radiation shield of claim 14, wherein the first and second parts in combination with the axially extendable section define opposing first and second cut-outs that are positioned and configured to accommodate spinal cord nerves when the body surrounds the spinal cord.

16. The radiation shield of claim 15, wherein the axially extendable section is disposed between the first and second cut-outs.

17. A radiation shield for use in treatment of a patient having spinal metastatic disease comprising:
a body that has a height and defines a hollow space that is configured to receive a spinal cord of the patient such that the body surrounds the spinal cord of the patient, the body including an axially extendable section that is adjustable along the height of the body so as increase a surface area of the shield by increasing the height of the body, the body being shaped to accommodate spinal cord nerves when implanted, wherein the axially extendable section has a first end that is coupled to a first part of the body and an opposite second end is coupled to the first part of the body, whereby the axially extendable section slidingly travels in a vertical direction along the first part so as to alter an overall height of the first part.

18. The radiation shield of claim 17, wherein the axially extendable section moves between a retracted position in which a greater portion of the axially extendable section overlies the body and an extended position in which less of the axially extendable section overlies the body, wherein in both the retracted and extended positions, the axially extendable section is in contact with the body along a transverse axis thereof.

19. The radiation shield of claim 17, wherein the body includes a bottom edge, the axially extendable section moves between a retracted position and an extended position in which the axially extendable section is disposed below the bottom edge.

20. The radiation shield of claim 17, wherein the axially extendable section is slidingly adjustable along the height of the body.

21. The radiation shield of claim 17, wherein an inner surface of the axially extendable section is configured and positioned to face the patient's spinal cord.

* * * * *